United States Patent
Druzgala et al.

(10) Patent No.: US 12,257,228 B2
(45) Date of Patent: Mar. 25, 2025

(54) CARDIOVERSION METHODS USING BUDIODARONE

(71) Applicant: Xyra, LLC, Santa Rosa, CA (US)

(72) Inventors: Pascal Druzgala, Santa Rosa, CA (US); Peter Gerard Milner, Mountain View, CA (US)

(73) Assignee: Xyra, LLC, Santa Rosa, CA (US)

( * ) Notice: Subject to any disclaimer, the term of this patent is extended or adjusted under 35 U.S.C. 154(b) by 0 days.

(21) Appl. No.: 18/351,261

(22) Filed: Jul. 12, 2023

(65) Prior Publication Data

US 2025/0009708 A1 Jan. 9, 2025

Related U.S. Application Data

(60) Provisional application No. 63/525,014, filed on Jul. 5, 2023.

(51) Int. Cl.
| | | |
|---|---|---|
| *A61K 31/343* | (2006.01) | |
| *A61K 31/4439* | (2006.01) | |
| *A61K 31/444* | (2006.01) | |
| *A61K 31/4545* | (2006.01) | |
| *A61K 31/5377* | (2006.01) | |
| *A61P 9/06* | (2006.01) | |

(52) U.S. Cl.
CPC ........ *A61K 31/343* (2013.01); *A61K 31/4439* (2013.01); *A61K 31/444* (2013.01); *A61K 31/4545* (2013.01); *A61K 31/5377* (2013.01); *A61P 9/06* (2018.01)

(58) Field of Classification Search
CPC ............................. A61K 31/343; A61P 9/06
See application file for complete search history.

(56) References Cited

U.S. PATENT DOCUMENTS

| | | | |
|---|---|---|---|
| 9,282,908 B2 | 3/2016 | Spector | |
| 9,549,912 B2 | 1/2017 | Milner et al. | |
| 11,759,640 B2 | 9/2023 | Druzgala et al. | |
| 2011/0136779 A1 | 6/2011 | Milner et al. | |
| 2011/0144199 A1* | 6/2011 | Milner | A61K 31/343 |
| | | | 514/469 |
| 2011/0269762 A1* | 11/2011 | Milner | A61K 31/352 |
| | | | 514/236.8 |
| 2013/0143861 A1 | 6/2013 | Milner et al. | |
| 2014/0309296 A1 | 10/2014 | Druzgala | |
| 2017/0354635 A1 | 12/2017 | Milner et al. | |
| 2018/0028086 A1 | 2/2018 | Cao et al. | |
| 2020/0323459 A1 | 10/2020 | Saha et al. | |
| 2023/0233863 A1 | 7/2023 | Druzgala et al. | |
| 2023/0355990 A1 | 7/2023 | Druzgala et al. | |
| 2023/0372284 A1 | 7/2023 | Druzgala et al. | |
| 2024/0033531 A1 | 2/2024 | Druzgala et al. | |

FOREIGN PATENT DOCUMENTS

| | | |
|---|---|---|
| WO | 2014143625 A1 | 9/2014 |
| WO | 2021163331 A1 | 8/2021 |
| WO | 2023133510 A1 | 7/2023 |

OTHER PUBLICATIONS

Arya et al. Europace, 2009, vol. 11, p. 458-464 (Year: 2009).*
Ezekowitz et al. J. Interv. Card. Electrophysiol., 2012, vol. 34, p. 1-9 (Year: 2012).*
Mischke, K., Knackstedt, C., Marx, N., & Vollmann, D. (2013). Insights into atrial fibrillation. Minerva medica, 104(2), 119-130. PMID 23514988.
Capucci A, et al. Monitored atrial fibrillation duration predicts arterial embolic events in patients suffering from bradycardia and atrial fibrillation implanted with antitachycardia pacemakers. J Am Coll Cardioll 2005;46:1913-1920.
Ezekowitz, M. D., Dimarco, J., Kaszala, K., Ellenbogen, K., Boddy, A., & Koren, A. A placebo-controlled, double-blind, randomized, multicenter study to assess the effects of dronedarone on atrial fibrillation burden in subjects with permanent pacemakers. J Interv Card Electrophysiol (2015) 42:69-76.
Glotzer, T. V. The Trends Study: is there a critical value of daily atrial tachyarrhytmia burden from device diagnostics that raises stroke risk. Circulation: Arrhythmia and Electrophysiology, vol. 2, Issue 5, Oct. 1, 2009: 474-480, https://ahajournals.org/doi/epub/1.1161/CIRCEP.109.849638.
Kirchhof P., Camm A. J., Goette A., Brandes A, Eckardt .L, Elvan A., et al. Early Rhythm-Control Therapy in Patients with Atrial Fibrillation. New England Journal of Medicine. 2020;383(14): 1305-16.
Munger, T. M.; Wu, L. Q.; Shen, W. K. Journal of Biomedical Research. 2014, 28 (1): 1-17. doi: 10.7555/JBR.28.20130191. PMC 3904170. PMID 24474959.
Gulizia, M.M., Cemin, R., Colivicchi, F., De Luca, L., Di Lenarda, A., Boriani, G., Di Pasquale, G., Nardi, F., Scherillo, M., Lucci, D. and Fabbri, G., "Management of atrial fibrillation in the emergency room and in the cardiology ward: the Blitz AF study." Ep Europace 2019; 21(2):230-238.
Perez M. V., Mahaffey K. W., Hedlin H., Rumsfeld J. S., Garcia A., Ferris T., et al. Large-Scale Assessment of a Smartwatch to Identify Atrial Fibrillation. New England Journal of Medicine. 2019;381(20):1909-17.
Wolf P. A, Abbott R. D., Kannel W. B. Atrial fibrillation as an independent risk factor for stroke: the Framingham Study. AHA Journals Stroke 1991; 22:983-988.
Zoni-Berisso, M.; Lercari, F.; Carazza, T.; Domenicucci, S. (2014). "Epidemiology of atrial fibrillation: European perspective". Clinical Epidemiology. 6: 213-20. doi:10.2147/CLEP.S47385. PMC 4064952. PMID 24966695.

(Continued)

*Primary Examiner* — James D. Anderson
(74) *Attorney, Agent, or Firm* — Banner & Witcoff, Ltd.

(57) ABSTRACT

Disclosed are cardioversion methods for patients with either paroxysmal or persistent AFib which methods use budiodarone or a pharmaceutical composition comprising budiodarone.

24 Claims, 2 Drawing Sheets
(2 of 2 Drawing Sheet(s) Filed in Color)

(56) References Cited

OTHER PUBLICATIONS

Jun. 23, 2023—(WO) International Search Report and Written Opinion—App PCT/US2023/060238.
PCT/US23/27521 filed Jul. 12, 2023.
Nov. 14, 2023—U.S. Non-final Office Action—U.S. Appl. No. 18/376,727.
Sep. 20, 2023—U.S. Non-final Office Action—U.S. Appl. No. 18/222,621.
Jan. 16, 2024—U.S. Non-final Office Action—U.S. Appl. No. 18/221,235.
Flaker, Greg C., et al., "Asymptomatic Atrial Fibrillation: Demographic Features and Prognostic Information from the Atrial Fibrillation Follow-Up Investigation of Rhythmic Management (AFFIRM) Study", American Heart Journal, Apr. 2005, pp. 657-663.
Go, Alan S., et al., "Association of Burden of Atrial Fibrillation With Risk of Ischemic Stroke in Adults With Paroxysmal Atrial Fibrillation, The KP-RHYTHM Study," JAMA Cardiology, 2018, 3(7):601-608.
Wojcikowski, Marek and Pankiewicz, Bogdan, "Photoplethysmographic time-domain heart rate measurement algorithm for resource-constrained wearable devices and its implementation," Sensors 20, No. 6 (2020): 1783.
Turakhia, Mintu P., Ziegler, Paul D. et al., "Atrial Fibrillation Burden and Short-Term Risk of Stroke: Case-Crossover Analysis of Continuously Recorded Heart Rhythm From Cardiac Electronic Implanted Devices," Circ Arrhythm Electrophysiol., 2015, 8(5):1040-7.
Singer, Daniel E., Ziegler, Paul D., Koehler, Jodi L., Sarkar, Shantanu and Passman, Rod S., "Temporal Association Between Episodes of Atrial Fibrillation and Risk of Ischemic Stroke," JAMA Cardiology, 6(12):1364-1369 (2021).
Apr. 5, 2024—(WO) International Search Report and Written Opinion—App PCT/US2023/027521.
Arya et al: "P2-76", Heart Rhythm, Elsevier, US, vol. 3, No. 5, May 1, 2006 (May 1, 2006), p. SI64, XP005483785, ISSN: 1547-5271, DOI: 10.1016/J.HRTHM.2006.02.488 abstract.
For the Pascal Investigators et al: "A randomized trial of budiodarone in paroxysmal atrial fibrillation", Journal of Interventional Cardiac Electrophysiology, Kluwer Academic Publishers, BO, vol. 34, No. 1, Dec. 29, 2011 (Dec. 29, 2011), pp. 1-9, XP035050015, ISSN: 1572-8595, DOI: 10.1007/S10840-011-9636-3, abstract Methods; Results figures 1-3, p. 7; left-hand column, paragraph 2, p. 7, right-hand column, last paragraph.
May 16, 2024—U.S. Final Office Action—U.S. Appl. No. 18/221,235.
"Report: More than 15,000 Adverse Events Linked to Xarelto in 2016", Market Insider. Published Jul. 25, 2017; as available Nov. 27, 2021 at <https://markets.businessinsider.com/news/stocks/report-more-than-15-000-adverse-events-linked-to-xarelto-in-2016-1002203317>, 14 pages. Archived Nov. 27, 2021 to, and retrieved Mar. 28, 2024 from, the Wayback Machine <https://web.archive.org/web/20211127004628/https://markets.businessinsider.com/news/stocks/report-more-than-15-000-adverse-events-linked-to-xarelto-in-2016-1002203317>.
"Pacemaker," Mayo Clinic. As available Oct. 28, 2021 to <https://www.mayoclinic.org/tests-procedures/pacemaker/about/pac-20384689>, 8 pages. Archived Oct. 28, 2021 to, and retrieved Mar. 28, 2024 from, the Wayback Machine <https://web.archive.org/web/20211028021506/https://www.mayoclinic.org/tests-procedures/pacemaker/about/pac-20384689>.
"Atrial Fibrillation—Treatment," NHS website. As available Dec. 24, 2021 at <https://www.nhs.uk/conditions/atrial-fibrillation/treatment/>, 6 pages. Archived Dec. 24, 2021 to, and retrieved Mar. 28, 2024 from, the Wayback Machine <https://web.archive.org/web/20211224221300/https://www.nhs.uk/conditions/atrial-fibrillation/treatment/>.
Aug. 27, 2024—(US) Final Office Action—U.S. Appl. No. 18/221,235.
Sep. 5, 2024—(US) Non-final Office Action—U.S. Appl. No. 18/618,822.
Oct. 16, 2024—(WO) International Search Report and Written Opinion—PCT/US24/36488.
Meng, Xu, et al.: "Bioavailability of amiodarone tablets administered with and without food in healthy subjects", American Journal of Cardiology, vol. 87, No. 4, 15, Feb. 2001 (Feb. 15, 2001), pp. 432-435, XP093210764.
Mar. 22, 2023—(US) Non-final Office Action—U.S. Appl. No. 17/978,835.
Dec. 1, 20246 - (US) Final Office Action - U.S. Appl. No. 18/221,235.
Lewalter, T., & Boriani, G. (2012). Relevance of monitoring atrial fibrillation in clinical practice. Arrhythmia & Electrophysiology Review, 1(1), 54.
Katritsis, D. G., Gersh, B. J., & Camm, A. J. (2015). Anticoagulation in atrial fibrillation-current concepts. Arrhythmia & Electrophysiology Review, 4(2), 100.

* cited by examiner

CARDIOVERSION METHODS USING BUDIODARONE

BACKGROUND

Field

This disclosure provides for methods to cardiovert patients with either paroxysmal or persistent atrial fibrillation (AFib) back to sinus rhythm which methods use a pharmaceutical composition comprising budiodarone.

RELATED APPLICATIONS

This application claims benefit of U.S. provisional application 63/525,014 filed on Jul. 5, 2023. The entire contents of which is incorporated by reference.

STATE OF THE ART

Patients suffering from paroxysmal or persistent AFib experiencing a prolonged episode of AFib are at elevated risk of a stroke and/or congestive heart failure. These risks increase as the duration of the episode extends. Patients with symptomatic paroxysmal or persistent AFib are significantly more likely to recognize their condition whereas asymptomatic patients on a heart rhythm monitor that provides an alarm-based warning of prolonged AFib will become aware of their condition once the alarm has been activated. In either case, many such patients presenting themselves at a hospital emergency room or are in a critical care unit with such an extended episode of AFib are treated by having a cardioversion procedure typically by stopping the heart and restarting it in order to restore sinus rhythm. Currently, there are from about 70,000 to perhaps as high as 100,000 or more cardioversions done each year with the number increasing as the population ages. These numbers represent a fraction of patients who present themselves in emergency rooms with AFib. One reference suggested that about 25% of patients presenting at the emergency room with AFib were treated with cardioversion. Gulizia et al., *Europace.* 2019; 21(2): 230-238. This suggests that some of the non-treated patients were contra-indicated for this procedure due to co-morbidities and some had their sinus rhythm restored without cardioversion.

The method of choice for cardioversion is electrical cardioversion, which relies upon stopping and restarting the heart to restore sinus rhythm. However, this procedure comes with several shortcomings. From the patient's perspective, there is a risk of dying during or within a few months after this procedure due to, for example, the release of blood clots from the heart during electrical cardioversion. From the clinician's perspective, electrical cardioversions require at least one or more nurses, an anesthesiologist, a cardiologist, the use of an anti-coagulant, and the like all at a significant cost to the health care system. From a cost perspective, cardioversion can cost thousands of dollars which, given the number of cardioversions conducted annually, imposes a significant cost burden on the healthcare system, particularly when the costs for treating patients who have a blood clot that releases during or shortly after the procedure or are included.

SUMMARY

Disclosed are methods to cardiovert a patient with an extended episode of paroxysmal or persistent AFib that utilizes a single high dose of budiodarone or a pharmaceutically acceptable salt thereof to effect cardioversion of the AFib sinus rhythm in said patient. The single high dose of budiodarone or a pharmaceutically acceptable salt thereof is preferably administered orally but other routes of administration are contemplated herein including intravenous, rectal, and pulmonary administration. The patient undergoing cardioversion is first deemed suitable for the procedure.

In one embodiment, there is provided a method for cardioverting a patient with paroxysmal or persistent AFib suffering from an extended episode of AFib, said method comprising: a) evaluating the patient to confirm that the patient has paroxysmal or persistent AFib and is suitable for cardioversion; b) administering budiodarone or a pharmaceutically acceptable salt thereof to said patient in an amount sufficient to effect cardioversion of said AFib back to sinus rhythm in said patient; and c) monitoring said patient subsequent to said administration to confirm that the patient is responsive to cardioversion.

In another embodiment, a method is provided for cardioverting a patient with paroxysmal or persistent AFib suffering from an extended episode of AFib and deemed suitable for cardioversion, said method comprising: a) administering of budiodarone or a pharmaceutically acceptable salt thereof to said patient in an amount sufficient to effect cardioversion of said AFib back to sinus rhythm, wherein the patient has been confirmed as having paroxysmal or persistent AFib as well as being deemed suitable for cardioversion; and b) monitoring said patient subsequent to said administration to confirm that the patient is responsive to cardioversion.

A further embodiment provides a method for cardioverting a patient with paroxysmal or persistent AFib suffering from an extended episode of AFib, said method comprising: a) administering a sufficient amount of budiodarone or a pharmaceutically acceptable salt thereof to said patient to achieve a plasma concentration of at least about 13 ng/mL for a period of time to cardiovert said patient back to sinus rhythm, wherein the patient has been confirmed as having paroxysmal or persistent AFib and deemed suitable for cardioversion; and b) monitoring said patient subsequent to said administration to confirm that the patient is responsive to cardioversion In another embodiment, a method is provided for cardioverting a patient with paroxysmal or persistent AFib suffering from an extended episode of AFib and deemed suitable for cardioversion, said method comprising:
a) administering budiodarone or a pharmaceutically acceptable salt thereof to said patient in an amount sufficient to effect cardioversion of said AFib back to sinus rhythm, wherein the patient has been confirmed as having paroxysmal or persistent AFib; and
b) monitoring said patient subsequent to said administration to confirm that the patient is responsive to cardioversion.

A further embodiment provides a method for cardioverting a patient with paroxysmal or persistent AFib suffering from an extended episode of AFib, said method comprising:
a) administering a sufficient amount of budiodarone or a pharmaceutically acceptable salt thereof to said patient to achieve a plasma concentration of at least about 13 ng/mL for a period of time to cardiovert said patient back to sinus rhythm, wherein the patient has been confirmed as having paroxysmal or persistent AFib and deemed suitable for cardioversion; and
b) monitoring said patient subsequent to said administration to confirm that the patient is responsive to cardioversion.

In one embodiment, the amount of budiodarone or a pharmaceutically acceptable salt thereof administered to said patient is sufficient to provide for sustained plasma concentration of at least about 13 ng/mL for a period of at least about 3 hours, at least about 4 hours, at least about 5 hours, or at least about 6 hours post-administration of budiodarone or a pharmaceutically acceptable salt thereof. Monitoring of the patient's heart rhythm is preferably continued during the entire period when the plasma concentration of budiodarone or a pharmaceutically acceptable salt thereof is maintained at about 13 ng/mL. In a preferred embodiment, the plasma concentration of budiodarone or a pharmaceutically acceptable salt thereof ranges from about 13 ng/mL up to a $C_{max}$ of about 350 ng/mL. In another preferred embodiment, the plasma concentration of budiodarone or a pharmaceutically acceptable salt thereof ranges from about 50 ng/mL to about 350 ng/mL and any subrange of about 10 ng within said range.

In one embodiment, budiodarone or a pharmaceutically acceptable salt thereof is administered orally, sublingually, intravenously (i.v. or IV), rectally, as an aerosol (pulmonary), or as an intranasal spray, or a combination thereof. In one preferred embodiment, budiodarone or a pharmaceutically acceptable salt thereof is administered orally using capsules, pills, or tablets. Given the efficiency of delivery, the amounts required to provide the plasma levels as presented above or herein, the dosing of budiodarone or a pharmaceutically acceptable salt thereof when given intravenously, sublingually, or in a spray may be in a lower dosage than that required for oral dosing.

As per the above, the methods described herein include the administration of budiodarone or a pharmaceutically acceptable salt thereof to the patient in an amount sufficient to cardiovert the AFib back to sinus rhythm when the plasma concentration of budiodarone or a pharmaceutically acceptable salt thereof is maintained at a level above as defined herein. In most cases, it is contemplated that cardioversion will be achieved for responsive patients within about 90 minutes, preferably within about 60 minutes, and more preferably within about 45, or within about 30 minutes after administration of budiodarone or a pharmaceutically acceptable salt thereof.

In general, the amount of budiodarone or a pharmaceutically acceptable salt thereof used to cardiovert the patient will be a single bolus oral dose of from about 400 mg to about 1,200 mg and preferably from about 800 mg to 1,200 mg. Preferably, each of these doses of budiodarone or a pharmaceutically acceptable salt thereof is administered as a single pill or capsule. In one preferred embodiment, the budiodarone or a pharmaceutically acceptable salt thereof dose to be used is selected by the clinician to achieve a $C_{max}$ of at least about 50 ng/mL or more which, based on its half-life data, is coupled with retaining a therapeutic plasma concentration of budiodarone of at least about 13 ng/mL for about 6 hours in the patient. Preferred dosages of budiodarone or a pharmaceutically acceptable salt thereof to achieve such prolonged retention of a therapeutic concentration include single doses of 800 mg, 1,000 mg, or 1,200 mg, or any dose between said 800 mg and 1,200 mg. Dosages of budiodarone or a pharmaceutically acceptable salt thereof may also be about 50 mg or about 100 mg amount interval increases between 400 mg to 1,200 mg (e.g., 1,100 mg or 700 mg). Sublingual, intravenous, rectal, and spray dosage forms of budiodarone would be less than 1,200 mg and are contemplated to range from about 10% to about 50% of the 1,200 mg dose used orally. Another aspect contemplates the administration of budiodarone or a pharmaceutically acceptable salt thereof via one or more means to the patient, e.g., via IV and oral, via sublingual and oral, via sublingual and spray, via oral and spray, via oral and IV, via IV and spray, or via IV and sublingual. It is contemplated that intravenous administration may induce a more rapid conversion to a sinus rhythm in the patient in need thereof.

In one embodiment, the administration of budiodarone or a pharmaceutically acceptable salt thereof is accompanied by the administration of a second drug such as a blood thinner (e.g., dabigatran, edoxaban, apixaban, or rivaroxaban—Xarelto®).

Also provided is a use of budiodarone or a pharmaceutically acceptable salt thereof to cardiovert a patient with paroxysmal or persistent AFib suffering from an extended episode of AFib.

Another embodiment provides administering a dose of budiodarone or a pharmaceutically acceptable salt thereof to a patient in need of cardioversion determined to have either paroxysmal or persistent AFib that is sufficient to produce an effective plasma level of >50 ng/ml in said patient within 60 min of administration, and maintaining a plasma level in said patient of >50 ng/ml for up to 6 hours thereby cardioverting a single sustained long episode of PAF, or a storm of long PAF episodes, or a persistent AFib episode back to normal sinus rhythm in said patient.

A further embodiment provides a use of budiodarone or a pharmaceutically acceptable salt thereof to cardiovert a patient with paroxysmal or persistent AFib suffering from an extended episode of AFib.

Yet another embodiment provides an oral dose of budiodarone or a pharmaceutically acceptable salt thereof for use in cardioverting a patient with paroxysmal or persistent AFib suffering from an extended AFib episode with an oral dose of budiodarone or a pharmaceutically acceptable salt thereof comprising from about 1,000 mg to about 2,000 mg. The oral dose of budiodarone or a pharmaceutically acceptable salt thereof can be delivered as a single bolus of about 1,000 mg, about 1,100 mg, about 1,200 mg, about 1,300 mg, about 1,400 mg, about 1,500 mg, about 1,600 mg, about 1,700 mg, about 1,800 mg, about 1,900 mg or about 2,000 and any 50 mg increment between 1,000 mg to about 2,000 mg. The dosage form of the administration of budiodarone or a pharmaceutically acceptable salt thereof of 1,000 mg to about 2,000 mg as described in this paragraph can be as a pill, a tablet, or a capsule.

In another embodiment, the pharmaceutically acceptable salt of budiodarone is budiodarone tartrate.

BRIEF DESCRIPTION OF DRAWINGS

The patent or application file contains at least one drawing executed in color. Copies of this patent or patent application publication with color drawing(s) will be provided by the Office upon request and payment of the necessary fee as required under 37 C.F.R. § 1.84.

DETAILED DESCRIPTION

Figure 1:
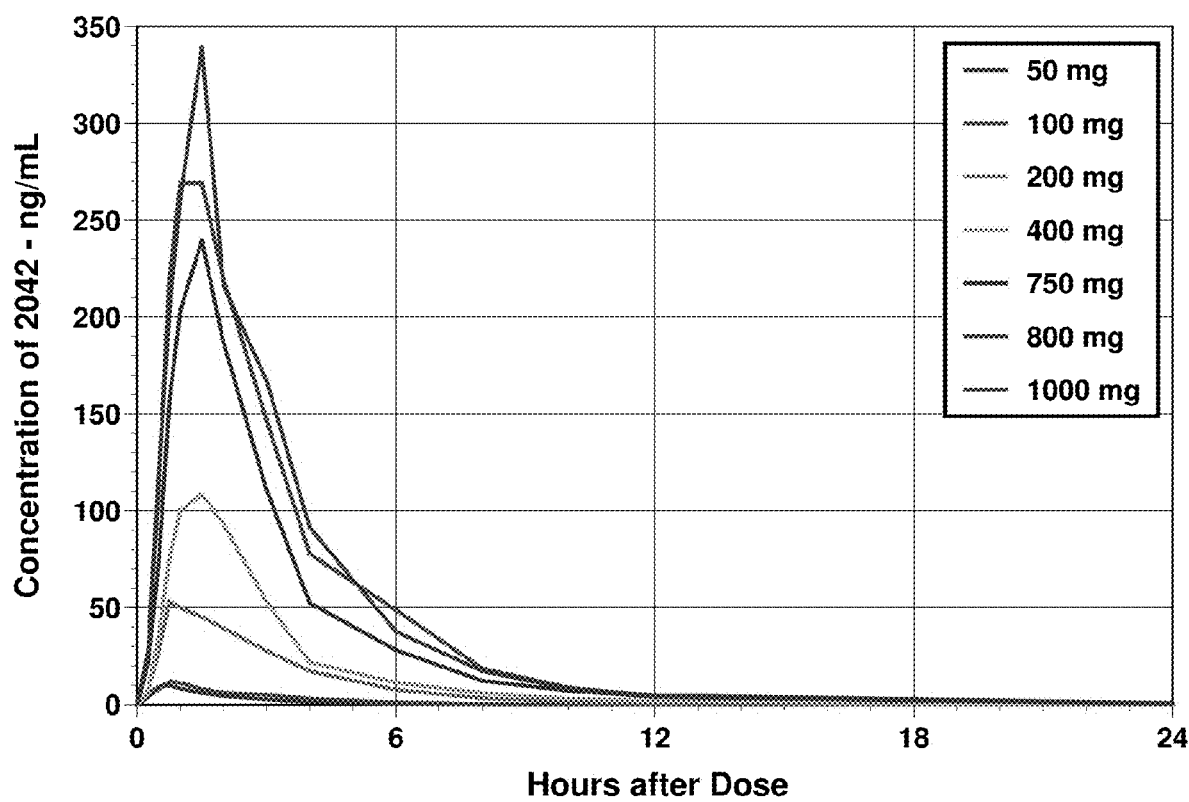
FIG. 1 illustrates the plasma concentration over time using different single-dose administrations of budiodarone. The data establishes that each single dose at or above 400 mg provided for a $C_{max}$ greater than 50 ng/mL and each maintained a concentration of greater than about 13 ng/mL for over 6 hours.

This disclosure is directed to methods for cardioverting AFib to sinus rhythm for patients with paroxysmal or persistent atrial fibrillation (AFib) and who are experiencing an extended period of AFib. The methods described herein employ budiodarone to cardiovert these patients. Terms that are not defined are given their definition in context or are given their medically acceptable definition.

The terminology used herein is for the purpose of describing particular embodiments only and is not intended to be limiting. As used herein, the singular forms "a", "an", and "the" are intended to include the plural forms as well, unless the context clearly indicates otherwise.

Definitions

As used herein, the term "optional" or "optionally" means that the subsequently described event or circumstance may or may not occur and that the description includes instances where the event or circumstance occurs and instances where it does not.

As used herein, the term "about" when used before a numerical designation, e.g., temperature, time, amount, concentration, and such other, including a range, indicates approximations that may vary by (+) or (−) 15%, 10%, 5%, 1%, or any subrange and/or value therebetween. Preferably, the term "about" when used with regard to a dose amount means that the dose may vary by +/−10%.

As used herein, the term "comprising" or "comprises" is intended to mean that the compositions or methods include the recited elements, but do not exclude others.

As used herein, the term "consisting essentially of" when used to define compositions and methods, shall mean excluding other elements of any essential significance to the stated purpose of the combination. Thus, a composition consisting essentially of the elements as defined herein, or a method consisting essentially of the protocol defined herein, would not exclude other components that do not materially affect the basic and novel characteristic(s) of the claimed subject matter.

As used herein, the term "consisting of" shall mean excluding more than trace elements of other ingredients or substantial method steps. Embodiments defined by each of these transition terms are within the scope of this disclosure.

As used herein, the term "AFib" or "atrial fibrillation" refers to all variants of atrial fibrillation except permanent AFib. Such variants include but are not limited to paroxysmal AFib, persistent AFib, as well as paroxysmal AFib and persistent AFib with low $CHA_2DS_2$-VASc scores (2 or less) and high $CHA_2DS_2$-VASc scores (3 or higher). $CHA_2DS_2$-VASc scores stand for congestive heart failure (C—1 pt), hypertension (H—1 pt), age ≥75 (A—2 pts), diabetes (D—1 pt), stroke (S—2 pt), vascular disease (V—1 pt), age 65 to 74 (A—1 pt), and sex category (Sc—1 pt for female) and are clinical prediction rules for estimating the risk of stroke in people with non-rheumatic atrial fibrillation (AF). A $CHA_2DS_2$-VASc score comprises 1 point or 2 points for each of the constituent risk factors, as indicated above As used herein, the term "extended duration of AFib" relates to the length of time an episode of AFib lasts in a patient. This length relates to the risk of stroke and/or heart failure. As is apparent, the longer the length of time a patient is in AFib, the higher the risk becomes. So, in one embodiment, an extended duration of AFib is any AFib episode lasting over at least about 30 minutes or at least about 1 hour or at least 5 hours, provided that the patient is not diagnosed as having permanent AFib.

As used herein, the term "paroxysmal AFib" refers to sporadic and intermittent episodes of AFib that last no more than 7 days before resolving back into sinus rhythm. Typically, but not necessarily, patients with de minimis AFib are also characterized as having paroxysmal AFib.

As used herein, the term "persistent AFib" refers to sporadic and intermittent episodes of AFib that last more than 7 days and may not resolve back into sinus rhythm without medical intervention (e.g., cardioversion).

As used herein, the term "budiodarone" refers to (S)-sec-butyl2-(3-(4-(2-(diethyl amino)ethoxy)-3,5-diiodobenzoyl) benzofuran-2-yl)acetate as well as pharmaceutically acceptable salts thereof. In some cases, budiodarone tartrate salt is referred to as ATI-2042 or just "2042". Budiodarone, as the free base, is represented by the following formula:

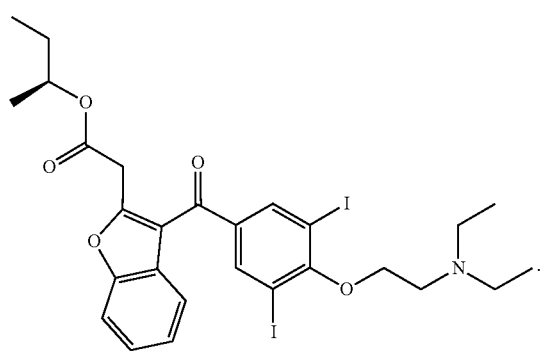 [SMILES: CC[C@H](C)OC(=O)Cc1oc2ccccc2c1C(=O)c1cc(I)c(OCCN(CC)CC)c(I)c1]

Pharmaceutically acceptable salts of the free base are included in the term "budiodarone") and include all approved pharmaceutically acceptable salts. Inclusive of acceptable salts of budiodarone are budiodarone tartrate or budiodarone citrate. In an embodiment, the pharmaceutically acceptable salt may be a polycarboxylic salt. As is appreciated in the art, the salt disassociates from the free base in vivo. In addition, the major metabolite of budiodarone is the deacylated compound—the free acid. Accordingly, in calculating the serum plasma level of budiodarone, the molecular weight of the free acid and the free base is used to determine molarity and concentration. In addition, when a salt other than the tartrate salt is administered, the dose of budiodarone tartrate salt that is used herein will necessarily be changed to reflect the molecular weight change due to the different salt.

Budiodarone has a combined mode of action and has been shown to reduce episodes of long-duration AFib without a significant increase in the QT interval. Budiodarone has a pattern of cardiac ion channel effects that are like amiodarone by design with enhanced late $Na^+$ channel blockade. Budiodarone's deliberately altered metabolism results in a much shorter half-life than amiodarone, however, enabling the avoidance of accumulation-related toxicities seen with amiodarone and complete inactivation and elimination from the body within hours to days of discontinuation.

As used herein, a "single high dose" refers to a dose of budiodarone that ranges from about 400 mg to about 1,200 mg which is administered in one or multiple dosing units or in a dosage form sufficient to achieve at least about 13 ng/mL budiodarone in a patient in need thereof. As noted above, a dosage form sufficient to achieve at least about 13 ng/mL budiodarone in a patient in need thereof could be less than about 1,200 mg when administered via inhalation, sublingually, or intravenously than when administered orally. A combination of these administration methods may be utilized and are contemplated when using the term "bolus". When multiple dosing units are employed, they can be administered concurrently with the other units such that the entire dose is administered within about 30 minutes and preferably within about 10 minutes. It is further noted that the patient may be asked to eat food, possibly and preferably fatty food, at the time of ingesting the bolus of budiodarone to achieve a more rapid intake of the drug into the system.

As used herein, "$C_{max}$" refers to the maximum plasma concentration of budiodarone after the administration of a single dose to a patient.

As used herein, a "suitable patient" or "patient" is a person who has been experiencing paroxysmal or persistent AFib for about 6 hours or less, or is a patient who has been experiencing paroxysmal or persistent AFib but has been determined to not have a blood clot through the use of a transesophageal echocardiogram or other means of confirming the absence of a blood clot in a patient, or the patient is known to have persistent or paroxysmal AFib and is on a blood thinner.

Methodology

The methods recited herein utilize a single high dose or bolus of budiodarone to cardiovert the patient suffering from an extended duration of AFib back to sinus rhythm. These methods are utilized with patients diagnosed with paroxysmal or persistent AFib. Patients with permanent AFib are not responsive to budiodarone and should be excluded by the attending physician from treatment with this drug. For those patients diagnosed with paroxysmal or persistent AFib, having an extended duration of AFib, and who present themselves to the emergency room or other facility capable of properly treating the patient, the clinician or caregiver confirms that the heart rhythm irregularity is AFib and not another known irregular heart rhythm and also determines that the patient is suitable for cardioversion.

Once confirmed, the attending clinician administers a single bolus (high) dose of budiodarone to the patient. The dose administered is sufficient to provide for a plasma concentration of budiodarone of at least about 13 ng/mL is maintained for at least about 3 hours and preferably for at least about 4 hours, or at least about 5 hours, or at least about 6 hours. In one preferred embodiment, the amount of budiodarone administered to the patient ranges comprises a single bolus of budiodarone at about 800 mg, or at least about 1,000 mg, or at least about 1200 mg. In some embodiments, the use of a high single dose of budiodarone is employed to provide rapid uptake to a therapeutic concentration in vivo. When so used, the plasma concentration of such doses will reach a $C_{max}$ of about 350 ng/mL or less and will maintain at least about 40 ng/mL or about 50 ng/mL for about 5+ hours or, in some cases, at least about 6 hours (see, FIG. 1). Regardless, such high dosing levels ensure that the plasma concentration remains over about 13 ng/mL and, in fact, over about 40 ng/mL, for up to about 6 hours.

Once the bolus of budiodarone is administered, the patient remains under observation in the emergency room, hospital room, or another urgent care facility while monitoring heart rhythm for a sufficient period to determine if the patient is responsive to budiodarone. Once the heart is restored to sinus rhythm and the plasma concentration of budiodarone is reduced to a satisfactory level, in the opinion of the attending clinician, the patient can be discharged provided that there are no other co-morbidities requiring further observation of the patient. In one preferred embodiment, such a level is below about 20 ng/mL and preferably below about 15 ng/mL. In one preferred embodiment, the patient is required to remain under observation for a short period of time (e.g., about 30 minutes to about 6 hours) to ensure that sinus rhythm is retained.

For those patients who are responsive to said methods, the patient can be discharged with a wearable that records and optionally transmits the heart rhythm to ascertain the extent and duration of AFib. For those patients who were non-responsive to said methods, these patients can be treated with electrical cardioversion.

Pharmaceutical Compositions

The specific dosing of budiodarone is accomplished by any number of accepted modes of administration including oral, intravenous, rectal, and pulmonary delivery. Pharmaceutical compositions compatible with each such delivery are well known in the art as are the methods useful in such delivery. Preferably, oral delivery is preferred typically using tablets, pills, capsules, and the like. The particular form used for oral delivery is not critical.

Pharmaceutical dosage forms of budiodarone may be manufactured by any of the methods well-known in the art, such as conventional mixing, tableting, encapsulating, and the like. The compositions as disclosed herein can include one or more physiologically acceptable inactive ingredients that facilitate the processing of active molecules into preparations for pharmaceutical use.

The compositions can comprise the drug in combination with at least one pharmaceutically acceptable excipient. Acceptable excipients are non-toxic, aid administration, and do not adversely affect the therapeutic benefit of the claimed compounds. Such excipient may be any solid, liquid, or semi-solid that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Other suitable pharmaceutical excipients and their formulations are described in REMINGTON'S PHARMACEUTICAL SCIENCES, edited by E. W. Martin (Mack Publishing Company, 18th ed., 1990).

The compositions as disclosed herein may, if desired, be presented in a single-use package. Such a package may, for example, comprise metal or plastic foil, such as a blister pack, a vial, or any other type of containment. The pack or dispenser device may be accompanied by instructions for administration including, for example, instructions for use.

The amount of the drug in a formulation can vary depending on the number of subunits required for the daily or periodic dose of the drug. Typically, the formulation will contain, on a weight percent (wt. %) basis, from about 10 to 99 wt. % of the drug based on the total formulation, with the balance being one or more suitable pharmaceutical excipients. Preferably, the compound is present at a level of about 20 to 70 wt. %.

EXAMPLES

The present disclosure is further understood by reference to the following examples, which are intended to be purely exemplary of this invention. The present disclosure is not limited in scope by the exemplified embodiments, which are intended as illustrations of single aspects of this disclosure only. Any functionally equivalent methods are within the scope of this disclosure. Various modifications of this invention in addition to those described herein will become apparent to those skilled in the art from the foregoing description and accompanying figures. Such modifications fall within the scope of the appended claims. In these examples, the following terms are used herein and have the following meanings. If not defined, the abbreviation has its conventional medical meaning.

It is noted that budiodarone concentrations used in the examples below include both the free acid and the free base versions of budiodarone.

The following abbreviations used herein have the following meanings. If not defined, the abbreviation will have its accepted meaning:

| AFib | = | Atrial Fibrillation |
| b.i.d. or bid | = | twice a day |
| Pk | = | pharmacokinetics |
| Hrs | = | Hours |
| mg | = | Milligrams |
| mL | = | Milliliter |
| ng | = | nanogram |

Example 1—Determination of the Minimum Concentration of Budiodarone to Reduce the Duration of Episodes of AFib In this example, patients were selected with long episodes of either paroxysmal or persistent AFib. Each of the patients was implanted with a pacemaker which monitored their heart rhythm. Patients were then evaluated for disease progression by monitoring their heart rhythm without budiodarone treatment in order to generate a baseline level of the duration of episodes of AFib. The baseline data was collected over two weeks. Patients were then given incremental doses of budiodarone at 200 mg b.i.d; 400 mg b.i.d.; 600 mg b.i.d.; and 800 mg b.i.d. where each dose was maintained for 2 weeks for a total of 4 treatment periods. A two-week washout period was employed after the completion of the 800 mg b.i.d. treatment period, wherein a washout period is the time after the last treatment to avoid misinterpreting observations about study-related treatments that may have been due to prior therapies. Pacemaker data were downloaded on days 8 and 14 of each two-week cycle and averages for each test period are shown. Blood was collected during each cycle and tested for the concentration of budiodarone. The results of this test are as follows:

| Dose | Baseline | 200 mg bid | 400 mg bid | 600 mg bid | 800 mg bid | washout |
|---|---|---|---|---|---|---|
| Average Episode duration | 4.8 hrs | 1.7 hrs | 0.6 hrs | 0.1 hrs | 0.5 hrs | 2.4 |
| Trough Pk levels ng/ml in plasma | — | 2.4 +/−0.9 | 5.2 +/−1.7 | 13.1 +/−5.6 | 19.8 +/−17.9 | 0.3 +/−0.4 |

Note that the duration of AFib in all dosing levels from 400 mg b.i.d. to 800 mg b.i.d. provided for maximum duration AFib levels of less than 90 minutes and, in fact, less than 60 and less than 45 minutes. In the case of 600 mg provided b.i.d., the longest average duration of AFib was 6 minutes (less than 30 minutes). It is also noted that the trough Pk levels of budiodarone are predicated on dosing approximately 12 hours apart and are not relevant to the trough levels at 6 hours post-administration.

This data supports the underlying basis that the administration of a bolus of budiodarone would rapidly reach $C_{max}$ plasma concentrations of at least 50 ng/mL and maintain as much for a sufficient period of time to effect cardioversion of a patient's AFib back to sinus rhythm. Note also the rapid removal of budiodarone from the blood such that the trough concentration in the plasma at 2 weeks post 800 mg budiodarone administered b.i.d. was 0.3 ng/mL in plasma or about 1.5% of the trough concentration of 19.8 ng/mL of budiodarone at the 800 mg dose b.i.d. showing rapid washout of the drug once stopped.

Example 2—Determination of Budiodarone Concentrations in Plasma Over Time Using Different Dosing Amounts of the Drug In this example, plasma concentrations of budiodarone were evaluated using different single-dosing amounts of the drug. Specifically, as illustrated in FIG. 1, budiodarone was administered to patients as a single dose at 50 mg, 100 mg, 200 mg, 400 mg, 600 mg, 800 mg, and 1000 mg. Each of the patients had blood draws taken and the concentration of budiodarone or its deacylated metabolite which is inactive. The resulting data was placed on a graph and the data for each concentration provided for both a $C_{max}$ for the dose employed as well as a trough value at 6 hours.

As to specifics, FIG. 1 establishes that the plasma concentration of a single dose of budiodarone at or above 400 mg provides for a $C_{max}$ greater than 50 ng/mL within 60 min or giving a single oral dose, and each maintained a plasma concentration of greater than about 13 ng/mL for over 6 hours. Still, further, a single dose of budiodarone at 800 mg or 1,000 mg will provide a plasma concentration of about 50 ng/mL at 6 hours and at least about 15 ng/mL at 8 hours.

The data also suggests that the use of a bolus of budiodarone such as 1,000 mg will provide for rapid uptake to a $C_{max}$ concentration of over 300 ng/mL in plasma which rapidly is eliminated to less than about 20 ng/mL in about 8 hours. In combination, the rapid uptake coupled with elimination in a short period of time renders such a bolus suitable for cardioversion as the high dosing of budiodarone will rapidly reach efficacious levels within 60 min of administration in vivo which is maintained at a plasma level above about 13 ng/mL for at least 6 hours followed by clearance from the body shortly thereafter. In combination, this data suggests that budiodarone will rapidly transition a long-duration episode of AFib to a significantly shorter episode or eliminates AFib, thereby cardioverting the patient into sinus rhythm within 90 minutes or less from the time the drug was administered.

As budiodarone has been established in clinical studies as being safe for in vivo administration, the use of budiodarone to cardiovert a patient is an alternative to electrical cardioversion and the corresponding issues associated therewith.

Example 3—the Impact of Food on the Concentration of Budiodarone

Figure 2:
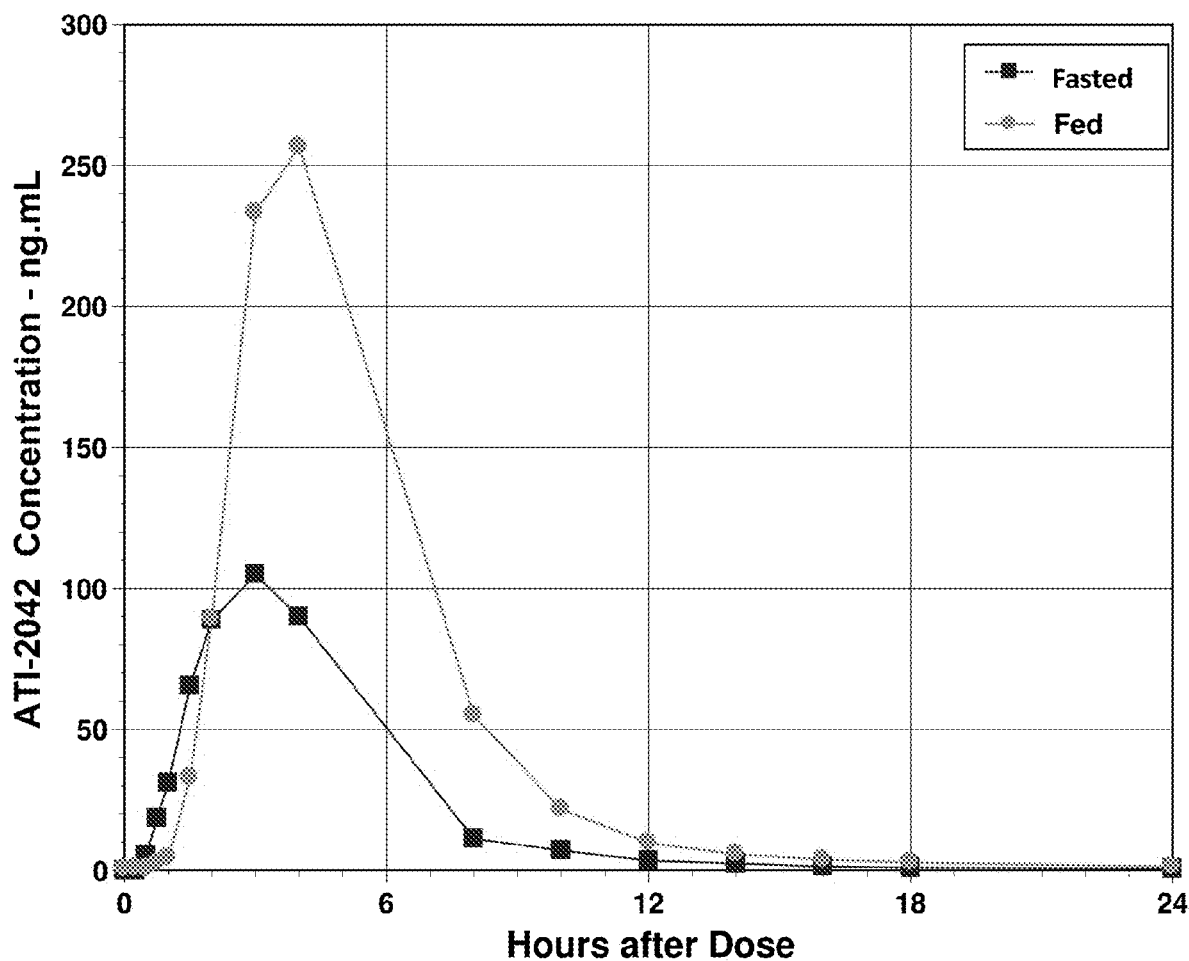
FIG. 2 illustrates the comparison of the plasma budiodarone concentrations between a fasting patent and a fed patient.

This example evaluates the impact on plasma budiodarone concentrations based on a fasting or fed patient. In this example, patients were either fasting or fed before the administration of budiodarone. After budiodarone administration, blood was collected from the patients, and the plasma concentration of budiodarone was determined. FIG. 2 illustrates that in the same dosing of budiodarone, the uptake of budiodarone increased as evidenced by the $C_{max}$ values. Note, however, that $C_{max}$ in the fed group is shifted to about an hour later in time than the $C_{max}$ in fasted patients. This suggests that fasting patients who are to undergo budiodarone cardioversion are preferably fed within about one hour (about 60 minutes) before the start of said cardioversion. This data shows that whether or not the drug is taken with food a single oral dose of 400-1,000 mg will achieve an effective plasma level of >50 ng/mL within 60 min and maintain that, and higher levels, for up to 6 hours thereby cardioverting back to normal sinus rhythm a single of a sustained long episode of PAF (paroxysmal atrial fibrillation) or persistent, or a storm of long AFib episodes that caused symptoms that brought the patient to the ER.

Embodiments

The following embodiments are contemplated.

[1] A method for cardioverting a patient with paroxysmal or persistent AFib suffering from an extended episode of AFib and deemed suitable for cardioversion, said method comprising: a) administering budiodarone or a pharmaceutically acceptable salt thereof to said patient in an amount sufficient to effect cardioversion of said AFib back to sinus rhythm, wherein the patient has been confirmed as having paroxysmal or persistent AFib; and b) monitoring said patient subsequent to said administration to confirm that the patient is responsive to cardioversion.

[2] A method for cardioverting a patient with paroxysmal or persistent AFib suffering from an extended episode of AFib, said method comprising: a) administering a sufficient amount of budiodarone or a pharmaceutically acceptable salt thereof to said patient to achieve a plasma concentration of said budiodarone or the salt thereof at least about 13 ng/mL for a period of time to cardiovert said patient back to sinus rhythm, wherein the patient has been confirmed as having paroxysmal or persistent AFib and deemed suitable for cardioversion; and b) monitoring said patient subsequent to said administration to confirm that the patient is responsive to cardioversion.

[3] The method of any one of Embodiments [1] or [2], wherein the amount of budiodarone or a salt thereof administered to said patient is sufficient to provide for a plasma concentration of from about 13 ng/mL to about 350 ng/mL in said patient, provided that the plasma concentration of budiodarone remains greater than at least about 13 ng/mL for at least 6 hours post-administration.

[4] The method of any one of Embodiments [1] or [3], wherein the amount of budiodarone or a salt thereof administered to said patient is sufficient to provide a plasma concentration of budiodarone or a salt thereof in said patient to about 50 ng/mL to about 350 ng/mL for at least about 5 hours post-administration.

[5] The method of Embodiment [4], wherein the amount of budiodarone or a salt thereof administered to said patient is sufficient to provide a plasma concentration of budiodarone or a salt thereof in said patient of about 50 ng/mL to about 350 ng/mL for at least about 6 hours.

[6] The method of any one of Embodiments [1]-[5], wherein said administration of the budiodarone or a salt thereof is oral, sublingual, intravenous, rectal, or an aerosol.

[7] The method of any one of Embodiments [1]-[6], wherein budiodarone or a salt thereof is administered orally using capsules, pills, or tablets.

[8] The method of any one of Embodiments [1]-[7], wherein said dose of budiodarone or a salt thereof is administered as a single dose of about 400 mg to about 2,000 mg.

[9] The method of Embodiment [8], wherein said dose of budiodarone or a salt thereof is administered as a single dose of about 800 mg to about 1,200 mg.

[10] The method of Embodiment [8], wherein said dose of budiodarone or a salt thereof is administered as a single dose of about 1,000 mg.

[11] The method of Embodiment [8], wherein said dose of budiodarone or a salt thereof is administered as a single dose of about 1,200 mg.

[12] The method of any one of Embodiments [1]-[11], which further comprises administering a blood thinner with the budiodarone or salt thereof to said patient, wherein the blood thinner is dabigatran, edoxaban, apixaban, or rivaroxaban.

[13] The method of any one of Embodiments [1]-[12], wherein cardioversion of said patient is accomplished in about 90 minutes or less from administering budiodarone or a salt thereof.

[14] The method of any one of Embodiments [1]-[12], wherein cardioversion is accomplished in about 60 minutes or less from administering budiodarone or a salt thereof.

[15] The method of any one of Embodiments [1]-[12], wherein cardioversion is accomplished in about 45 minutes or less from administering budiodarone or a salt thereof.

[16] The method of any one of Embodiments [1]-[12], wherein cardioversion is accomplished in about 30 minutes or less from administering budiodarone or a salt thereof.

[17] The method of any one of Embodiments [1]-[12], wherein said patient is fed about 1 hour or less prior to administering budiodarone or a salt thereof.

[18] A kit comprising a single dose of budiodarone or a pharmaceutically effective salt thereof that is effective in cardioverting a patient and instructions for post-administration monitoring of the patient.

[19] Administering a dose of budiodarone or a pharmaceutically acceptable salt thereof to cardiovert a patient determined to have either paroxysmal or persistent Afib, wherein said administered dose produces an effective plasma level of >50 ng/ml in said patient within about 60 min of administration, and maintaining a plasma level in said patient of >50 ng/ml for up to about 6 hours thereby cardioverting a single sustained long episode of PAF, or a storm of long PAF episodes, or a persistent AFib episode that caused symptoms back to normal sinus rhythm in said patient.

[20] A use of budiodarone or a pharmaceutically acceptable salt thereof to cardiovert a patient with paroxysmal or persistent AFib suffering from an extended episode of AFib by administering a dosage of budiodarone according to any one of the methods of Embodiments [1]-[19].

[21] An oral dose of budiodarone or a pharmaceutically acceptable salt thereof of Embodiment [20] comprising from about 1,000 mg to about 2,000 mg in a single dosage unit.

[22] An oral dose of budiodarone or a pharmaceutically acceptable salt thereof of Embodiment [20] comprising about 900 mg, about 1,000 mg, about 1,100 mg, or about 1,200 mg in a single dosing unit.

[23] The oral dose of budiodarone of any of Embodiments [21]-[22], wherein said dosing unit is a pill, a capsule, or a tablet.

[24] The oral dose of budiodarone or a pharmaceutically acceptable salt of any of Embodiments [20] to [23], wherein the budiodarone salt is budiodarone tartrate.

What is claimed is:

1. A method for cardioverting a patient having an extended episode of paroxysmal or persistent AFib and who is deemed suitable for cardioversion, said method comprising:

a) administering a single oral dose of budiodarone or a pharmaceutically acceptable salt thereof to said patient in an amount from about 900 mg to about 2,000 mg, wherein the amount is sufficient to provide for a peak budiodarone blood plasma concentration in said patient of at least about 50 ng/mL and maintain a budiodarone blood plasma concentration in said patient of at least about 13 ng/mL for at least 6 hours wherein said patient's AFib heart rhythm cardioverts to sinus rhythm; and b) monitoring a heart rhythm of said patient, subsequent to said administering, until the budiodarone blood plasma concentration is measured to be below about 20 ng/mL.

2. A method for inducing cardioversion in a patient diagnosed with either paroxysmal or persistent AFib and suffering from an episode of AFib, said method comprising:
a) administering, based on a determination that said patient is suitable for cardioversion, a single oral dose of from about 900 mg to about 2,000 mg of budiodarone or a pharmaceutically acceptable salt thereof to said patient to achieve a budiodarone blood plasma concentration of at least about 13 ng/mL for a period of at least 6 hours, wherein the single oral dose comprises one or more unit doses and the administration of the single oral dose is performed within a 30 minute time period, and wherein the determination that said patient is suitable for cardioversion comprises
determining one or more of:
that said patient is experiencing an AFib episode deemed suitable for cardioversion;
that data confirms an absence of blood clots in said patient; or
that said patient is on a blood thinner; and
b) monitoring said patient subsequent to said administration to confirm that the patient is responsive to and maintains cardioversion.

3. The method of claim 2, wherein an amount of budiodarone or the pharmaceutically acceptable salt thereof in said single oral dose is sufficient to provide for a peak budiodarone blood plasma concentration of at least about 300 ng/mL in said patient.

4. The method of claim 3, wherein the amount of budiodarone or the pharmaceutically acceptable salt thereof in said single oral dose is sufficient to provide for the budiodarone blood plasma concentration in said patient to be at least about 50 ng/mL for at least about 5 hours.

5. The method of claim 4, wherein the amount of budiodarone or the pharmaceutically acceptable salt thereof in said single oral dose is sufficient to provide for the budiodarone blood plasma concentration in said patient to be at least about 50 ng/mL for at least about 6 hours.

6. The method of claim 2, wherein said budiodarone or the pharmaceutically acceptable salt thereof is administered orally using capsules, pills, or tablets.

7. The method of claim 2, wherein said budiodarone or the pharmaceutically acceptable salt thereof is administered to said patient in a single oral dose of from about 900 mg to about 1,200 mg.

8. The method of claim 2, wherein said budiodarone or the pharmaceutically acceptable salt thereof is administered as a single oral dose of about 1,000 mg.

9. The method of claim 2, wherein said budiodarone or the pharmaceutically acceptable salt thereof is administered as a single oral dose of about 1,200 mg.

10. The method of claim 2, which further comprises administering a blood thinner with said budiodarone or the pharmaceutically acceptable salt thereof, wherein the blood thinner comprises one or more of dabigatran, edoxaban, apixaban, or rivaroxaban.

11. The method of claim 2, wherein cardioversion is accomplished in about 90 minutes or less from the administration of said budiodarone or the pharmaceutically acceptable salt thereof.

12. The method of claim 11, wherein cardioversion is accomplished in about 60 minutes or less from the administration of said budiodarone or the pharmaceutically acceptable salt thereof.

13. The method of claim 11, wherein cardioversion is accomplished in about 45 minutes or less from the administration of said budiodarone or the pharmaceutically acceptable salt thereof.

14. The method of claim 11, wherein cardioversion is accomplished in about 30 minutes or less from the administration of said budiodarone or the pharmaceutically acceptable salt thereof.

15. The method of claim 2, wherein said patient is fed about 1 hour or less before the administration of said budiodarone or the pharmaceutically acceptable salt thereof.

16. The method of claim 2, wherein said budiodarone or the pharmaceutically acceptable salt thereof comprises budiodarone tartrate.

17. A kit of parts comprising:
a single oral unit dose of from about 900 mg to about 2,000 mg of budiodarone or a pharmaceutically acceptable salt thereof, and
instructions for post-administration monitoring of a heart rhythm of a patient at least until a plasma concentration of budiodarone in said patient goes below 20 ng/mL.

18. A method for cardioverting a patient back to normal sinus rhythm, said method comprising:
administering, based on a determination that said patient is in need of cardioversion and is determined to have either paroxysmal or persistent atrial fibrillation (AFib), a single oral dose comprising at least about 900 mg of budiodarone or a salt thereof to the patient.

19. The method of claim 18, wherein said single oral dose comprises at least about 1,000 mg to about 2,000 mg.

20. The method of claim 18, wherein said single oral dose comprises at least about 900 mg to 1,200 mg in a single dosing unit.

21. The method of claim 20, wherein said single dosing unit is a pill, a capsule, or a tablet.

22. The method of claim 18, wherein the budiodarone salt is budiodarone tartrate.

23. The method of claim 18, further comprising monitoring a heart rhythm of said patient after the administration of said single oral dose.

24. The method of claim 23, wherein the monitoring is continued until a budiodarone blood plasma concentration of said patient is measured to be below about 20 ng/mL and until said patient's heart rhythm cardioverts to sinus rhythm.

* * * * *